(12) United States Patent
Wittchow

(10) Patent No.: US 8,927,002 B2
(45) Date of Patent: Jan. 6, 2015

(54) STENT WITH A COATING OR A BASIC BODY CONTAINING A LITHIUM SALT AND USE OF LITHIUM SALTS FOR PREVENTION OF RESTENOSIS

(75) Inventor: Eric Wittchow, Nuremberg (DE)

(73) Assignee: Biotronik VI Patent AG, Baar (CH)

( * ) Notice: Subject to any disclaimer, the term of this patent is extended or adjusted under 35 U.S.C. 154(b) by 76 days.

(21) Appl. No.: 12/477,093

(22) Filed: Jun. 2, 2009

(65) Prior Publication Data

US 2009/0311300 A1 Dec. 17, 2009

(30) Foreign Application Priority Data

Jun. 17, 2008 (DE) .......................... 10 2008 002 471

(51) Int. Cl.
| | | |
|---|---|---|
| A61F 2/00 | (2006.01) |
| A01N 25/08 | (2006.01) |
| A01N 25/26 | (2006.01) |
| A61F 13/00 | (2006.01) |
| A01N 59/00 | (2006.01) |
| A01N 37/00 | (2006.01) |
| C07C 61/00 | (2006.01) |
| A61L 31/14 | (2006.01) |
| A61L 31/02 | (2006.01) |
| A61L 31/08 | (2006.01) |

(52) U.S. Cl.
CPC .............. *A61L 31/148* (2013.01); *A61L 31/028* (2013.01); *A61L 31/088* (2013.01)
USPC ........... 424/423; 424/409; 424/421; 424/422; 424/722; 514/557; 562/400

(58) Field of Classification Search
None
See application file for complete search history.

(56) References Cited

U.S. PATENT DOCUMENTS

| | | | |
|---|---|---|---|
| 2003/0103945 A1* | 6/2003 | Chen et al. .................... 424/93.7 |
| 2004/0247561 A1* | 12/2004 | Seo et al. ..................... 424/78.27 |
| 2005/0025804 A1* | 2/2005 | Heller ........................... 424/423 |
| 2005/0220835 A1* | 10/2005 | Jayaraman et al. ............ 424/423 |
| 2006/0120994 A1* | 6/2006 | Cotton et al. ............... 424/78.37 |
| 2007/0135908 A1 | 6/2007 | Zhao |
| 2008/0033536 A1* | 2/2008 | Wittchow .................... 623/1.38 |
| 2008/0033537 A1* | 2/2008 | Tittelbach ................... 623/1.42 |
| 2010/0114304 A1 | 5/2010 | Craig |
| 2013/0073028 A1 | 3/2013 | Chiba |

FOREIGN PATENT DOCUMENTS

| | | | |
|---|---|---|---|
| EP | 1270026 A1 * | 1/2003 |
| EP | 1655384 A1 | 5/2006 |
| EP | 1 795 215 A2 | 6/2007 |
| EP | 2551363 A1 | 1/2013 |
| WO | 9835067 A1 | 8/1998 |
| WO | WO 2008/086794 A2 | 7/2008 |
| WO | 2011118615 A1 | 9/2011 |
| WO | 2012068358 A1 | 5/2012 |

OTHER PUBLICATIONS

Stone, Gregg W., et al., N. Engl J Med 2004; 350;221-231 (pp. 1-76).*
Dasnurkar, Anup, Drug Loaded Polymeric Blends for Developing Vascular Stents, Aug. 2006, pp. 1-129.*
Dehpour, A. R., et al., The effect of Lithium on Endothelial-dependent Relaxation in Rat Isolated Aorta, Gen. Pharmac. vol. 26, No. 5 (1995), pp. 1003-1007.*
Medical Dictionary, vasodilation, (accessed Sep. 21, 2011), pp. 1-2.*
DE 10 2005 018 356 machine translation, (translated Sep. 21, 2011), pp. 1-5.*
European Search Report for EP 09 16 0151, (Feb. 23, 2010).
EPO Search Report for EP 13167767.6, (Sep. 18, 2013).

* cited by examiner

*Primary Examiner* — Ernst V Arnold
*Assistant Examiner* — Kyung Sook Chang
(74) *Attorney, Agent, or Firm* — Wagenknecht IP Law Group PC

(57) ABSTRACT

The invention relates to a stent with in particular a coated basic body made of an implant material the use of lithium salts as a coating material or a component of an implant material for stents and the use of lithium salts in a method for restenosis prevention. The inventive stent having a basic body made of an implant material is characterized in that (i) the basic body has a coating which comprises or consists of a lithium salt, and/or (ii) the implant material is biocorrodible and the basic body contains a lithium salt.

14 Claims, No Drawings

STENT WITH A COATING OR A BASIC BODY CONTAINING A LITHIUM SALT AND USE OF LITHIUM SALTS FOR PREVENTION OF RESTENOSIS

CROSS REFERENCE TO RELATED APPLICATIONS

This application claims benefit of priority to German patent application serial no. DE 10 2008 002 471.6 filed on Jun. 17, 2008; the contents of which are herein incorporated by reference in their entirety.

TECHNICAL FIELD

The invention relates to a stent with a basic body, optionally coated, made of an implant material, the use of lithium salts as a coating material or as a component of an implant material for stents and the use of lithium salts in a method for prevention of restenosis.

BACKGROUND OF THE INVENTION

The implantation of stents has become established as one of the most effective therapeutic measures in the treatment of vascular diseases. The purpose of stents is to assume a supporting function in hollow organs in a patient. Stents of a traditional design therefore have a tubular basic body with a filigree supporting structure of metallic struts, which is present initially in a compressed form for introduction into the body and then is widened at the site of application. One of the main areas of application of such stents is for permanent or temporary widening of vascular stenoses and maintaining their patency, in particular for widening occlusions (stenoses) in the coronary vessels. In addition, there are also known aneurysm stents which serve to support damaged vascular walls.

The basic body of the stent consists of an implant material. An implant material is a nonviable material, which is used for an application in medicine and enters into an interaction with biological systems. The basic prerequisites for use of a material as an implant material which comes in contact with the environment of the body when used as intended is its biocompatibility. Biocompatibility is understood to be the ability of a material to induce an appropriate tissue reaction in a specific application. This includes adaptation of the chemical, physical, biological and morphological surface properties of an implant to the recipient tissue with the goal of a clinically desired interaction. The biocompatibility of the implant material also depends on the chronological course of the reaction of the biosystem in which it is implanted. Thus relatively short-term irritation and inflammation occur and may lead to tissue changes. Biological systems thus react in various ways as a function of the properties of the implant material. Implant materials may be subdivided into bioactive, bioinert and degradable/absorbable materials, depending on the reaction of the biosystem.

A biological reaction to implant materials depends on the concentration, the duration of action and how it is supplied. The presence of an implant material alone often leads to inflammation reactions that may be triggered by mechanical stimuli, chemical substances as well as metabolic products. The inflammation process is usually accompanied by migration of neutrophilic granulocytes and monocytes through the vascular walls, migration of lymphocyte effecter cells with the formation of specific antibodies to the inflammation stimulus, activation of the complement system with the release of complement factors, which act as mediators, and ultimately the activation of blood coagulation. An immunological reaction is usually closely associated with an inflammation reaction and may lead to sensitization and the development of an allergy. An essential problem with implantation of stents in blood vessels is in-stent restenosis due to an overshooting neointimal growth, which is caused by a marked proliferation of arterial smooth muscle cells and a chronic inflammatory reaction.

One promising approach toward solving the problem is to use biocorrodible metals and their alloys as an implant material because a permanent supporting function of the stent is not usually necessary. The body tissue, which is initially damaged, regenerates. For example, DE 197 31 021 A1 proposes that medicinal implants should be made of a metallic material, the main components of which are iron, zinc or aluminum and/or an element from the group of alkali metals or alkaline earth metals. Alloys based on magnesium, iron and zinc are described as being especially suitable. Secondary components of the alloys may be manganese, cobalt, nickel, chromium, copper, cadmium, lead, tin, thorium, zirconium, silver, gold, palladium, platinum, silicon, calcium, lithium, aluminum, zinc and iron. In addition, DE 102 53 634 A1 describes the use of a biocorrodible magnesium alloy containing >90% magnesium, 3.7-5.5% yttrium, 1.5-4.4% rare earth metals and <1% remainder, this alloy being suitable in particular for production of an endoprosthesis, e.g., in the form of a self-expanding or balloon-expandable stent. The use of biocorrodible metallic materials in implants should lead to a definite reduction in rejection reactions or inflammation reactions.

It is also known that a higher measure of biocompatibility and thus an improvement in the restenosis rate can be achieved if implant materials are provided with coatings of tissue-compatible materials in particular. These materials are usually of an organic or synthetic polymer nature and in some cases are of natural origin.

If biocorrodible polymers are used the implant material or as the coating material, it should be noted that the products of degradation of these polymers, which are often acidic, can lead to an inflammatory reaction in the surrounding tissue, i.e., the material has only a moderate biocompatibility. For example, it has been proven that with biodegradable poly (ortho esters), neither the monomers nor the intermediate products during degradation are responsible for the inflammation but instead the acetic acid released in traces is responsible (Zignani et al., Subconjunctival biocompatibility of a viscous bioerodible poly(ortho ester), J. Biomed. Water. Res., 1997, 39 pp. 277-285). In addition to the unwanted biological response to the acidic degradation products, the altered pH in the case of an implant of a biocorrodible magnesium alloy with a coating of such a polymer also influences the degradation properties of the alloy: the acidic environment accelerates the degradation. Therefore, a stent made of a biocorrodible magnesium alloy, for example, loses its supporting power more rapidly.

According to another strategy for preventing restenosis, proliferation is to be inhibited by medication. Drug-coated stents (also known as DES. i.e., drug-eluting stents) in which the drugs have been proven to suppress the proliferation of smooth human vascular muscle cells are also known; examples include the drugs sirolimus and paclitaxel. One disadvantage is the concomitant medication required to prevent a late thrombosis, the high cost of the drugs used so far for the purpose of prevention of a restenosis as well as their complex processing.

BRIEF SUMMARY OF THE INVENTION

The object of the invention is to reduce or overcome one or more of the disadvantages of the state of the art described herein.

The invention is directed towards a stent having a basic body made of an implant material and its use. The inventive stent is characterized in that (i) the basic body has a coating consisting of or comprises a lithium salt; and/or (ii) the implant material is biocorrodible and the basic body contains a lithium salt.

The lithium salt may be basic and in some embodiments is be selected from the group consisting of lithium carbonate, lithium bicarbonate, lithium hydroxide, lithium nitride and a lithium salt of a carboxylic acid compound.

The implant material may be a biocorrodible magnesium alloy or a biocorrodible polymer. Exemplary biocorrodible polymers include a polymer whose degradation leads to an acidic degradation product, a polyester, a polyamide or a polyanhydride.

The stent may have a coating consisting essentially of a polymeric carrier matrix with embedded lithium salt or may contain these components. In these embodiments the carrier material may be a biocorrodible polymer whose degradation leads to an acidic degradation product. In further embodiments the biocorrodible polymer may be a polyester, a polyamide or a polyailihydride.

In another aspect of the present invention use of a lithium salt as a coating material for a stent is provided. In some embodiments use includes providing a stent and coating the stent with a coating material comprising a lithium salt. In other embodiments use includes coating an implantable material with a coating comprising a lithium salt and forming a stent.

In yet another aspect of the present invention use of a lithium salt as an additive for a stent made of a biocorrodible implant material is provided. In some embodiments use may include providing a biocorrodible implant material, which includes an additive including a lithium salt and forming a stent. In some embodiments use includes providing a biocorrodible implant material in the form of a stent and adding a lithium salt.

In still another aspect of the present invention lithium salt for use in a method for prevention of a restenosis is provided. In some embodiments a subject in need of preventing restenosis is identified and a lithium salt in an amount sufficient to prevent restenosis is administered. Administration may be by suitable means including implanting a stent coated with a lithium salt or implanting a stent including a biocorrodible material and a lithium salt.

DETAILED DESCRIPTION OF THE INVENTION

The invention is directed to a stent having a basic body made of an implant material. The inventive stent is characterized in that (i) the basic body has a coating consisting of or containing a lithium salt, and/or (ii) the implant material is biocorrodible and the basic body contains a lithium salt.

It has been found that lithium salts have a dilating effect on blood vessels. This vasodilation has a positive influence on the diameter of the blood vessel in the vicinity of the lesion, which is supported by the stent (A. R. Dehpour, H. Aghadadashi. P. Ghafourifar, F. Roushanazamir, M. H. Ghahremani. F. Meysamee, N. Rassace, A. Koucharian, Effect of chronic lithium administration on endothelium-dependent relaxation in rat aorta. *Clin Fxp Pharmacol*. 2000 January-February; 27 (1-2): 55-9). Lithium salts have long been used for treatment of psychological disorders, e.g., bipolar affect disorders, mania and depression. In empirical studies, a relationship between the administration of lithium and a decline in the incidence of cancer has been demonstrated (Y. Cohen, A. Chemit, Y. Cohen, P. Sirota, B. Modan, Cancer morbidity in psychiatric patients: Influence of lithium carbonate treatment. *Med Oncol*. 1998 April; 15 (1): 32-6). The latter effect is most probably based on the influence on inositol metabolism by inhibiting myo-inositol-1-phosphatase, while inhibiting glycogen synthase kinase-3 (GSK-3) in nerve cells (M. J. Berridge, Inositol triphosphate and diacylglycerol as second messenger. *Biochem J* 1984 Jun. 1; 220 (2): 345-60, D. H. Carney, D. L. Scott, E. A. Gordon, E. F. LaBelle. Phosphoinositides in mitogenesis: neomycin inhibits thrombin-simulated phosphoinositide turnover and initiation of cell proliferation. *Cell*. 1985 September; 42 (2): 479-88, R. Williams, W. J. Ryves, E. C. Daltin, B. Eickholt, G. Shaltiel, G. Agam, A. J. Harwood, A molecular cell biology of lithium. *Biochem Soc Trans*. 2004 November; 32 (Pt 5): 799-802). In cell culture experiments, lithium chloride significantly suppresses the proliferation of various prostate cancer cell lines by reducing gene expression in the S-phase of the cell cycle (A. Sun, I. Shanmugam, J. Song, P. F. Terranove, J. B. Thrasher, B. Li, Lithium suppresses cell proliferation by interrupting E2F-DANN interaction and subsequently reducing S-phase gene expression in prostate cancer. *Prostate*. 2007 Jun. 15; 67 (9): 976-88). It also causes increased secretion of certain interleukins (IL-15; IL-8).

Due to the high local concentration of lithium ions in the stented lesion according to the invention, the cell cycle is stopped in the S-phase, so that restenosis is prevented because mainly rapidly dividing cells are affected. One advantage of using lithium salts is the simple processability of these compounds in comparison with most organic drugs which are used for the same purposes. Furthermore, the costs of such lithium compounds amount to only a fraction of the cost of organic cytotoxic drugs such as sirolimus or paclitaxel. Therefore, another aspect of the invention lies in the use of lithium salts in a method for prevention of restenosis.

The dose of the lithium salt depends on many factors such as the site of implantation, the site of the lesion, the geometry and the materials used for the implant as well as the general condition of the patient himself. A local lithium ion concentration of 5 to 30 mmol/liter, more preferably from 15 to 25 mmol/liter should be achieved in the blood vessel. To achieve this, the stent is coated with 50 to 50 µg of a lithium salt per mm of stent length, or a degradable stent basic body is produced so that it contains 1 to 15 wt % lithium ions, corresponding to a total lithium content of 5 to 200 µg per mm stent length.

According to a first variant, the basic body has a coating which consists of or contains a lithium salt. A coating in the sense of this invention is an application of the components of the coating to the basic body of the stent in at least some sections. The entire surface of the basic body of the stent is preferably covered by the coating. The layer thickness is preferably in the range of 1 nm to 100 µm, especially preferably 300 nm to 15 µm. The coating consists of a lithium salt or contains such a lithium salt. The amount by weight of lithium salt in the components of the coating forming the coating is preferably at least 10%, especially preferably at least 30%. The coating may be applied directly to the surface of the implant. The processing may be performed by standard methods for coating. Single-layer or multilayer systems (e.g., so-called base coat, drug coat or top coat layers) may be created.

In addition to the lithium salt, which is essential to the present invention, the coating may also contain other components, in particular a polymer carrier matrix in which the lithium salt is embedded in a finely dispersed form. In other words, the stent has a coating consisting of a polymer carrier matrix with embedded lithium salt or containing these components. The carrier matrix may in particular contain other pharmaceutical drugs, X-ray markers or magnetic resonance markers.

According to a second variant, the basic body of the stent consists of a biocorrodible implant material and this basic body contains the lithium salt. When the stent is used as intended, the basic body made of the biocorrodible implant material is gradually degraded. The lithium salt is released in this process and can manifest the desired pharmacological effect in the area of the lesion. The biocorrodible implant material is usually a metallic or polymeric implant material.

Biocompatible metals and metal alloys for permanent implants comprise, for example, stainless steels (e.g. 316L), cobalt base alloys (e.g., CoCrMo casting alloys, CoCrMo forging alloys, CoCrWNi forging alloys and CoCrNiMo forging alloys), pure titanium and titanium alloys (e.g., cp titanium, TiAl6V4 or TiAl6Nb7) and gold alloys. In the field of biocorrodible stents, it is preferable to use magnesium or pure iron and biocorrodible base alloys of the elements magnesium, aluminum, zinc, iron and tungsten. The use of a biocorrodible magnesium alloy is especially preferred.

A biocorrodible magnesium alloy is understood to be a metallic structure in which the main component is magnesium. The main component is the alloy component which is present in the largest amount by weight in the alloy. The amount of the main component is preferably more than 50 wt %, in particular more than 70 wt %. The biocorrodible magnesium alloy preferably contains yttrium and other rare earth metals because such an alloy excels due to its physicochemical properties and high biocompatibility in particular also its degradation products. A magnesium alloy that is especially preferred for use has the composition 5.2-9.9 wt % rare earth metals, including 3.7-5.5 wt % yttrium and <1 wt % remainder, with magnesium accounting for the remainder of the alloy up to 100 wt %. The special suitability of this magnesium alloy has already been confirmed experimentally and in preliminary clinical trials, i.e. it has a high biocompatibility, favorable processing properties, good mechanical characteristics and an adequate corrosion behavior for the intended uses. The umbrella term "rare earth metals" is understood in the present case to include scandium (21), yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71).

The composition of the magnesium alloy is to be selected so that it is biocorrodible. The test medium for testing the corrosion behavior of alloys is synthetic plasma such as that specified for biocorrosion tests under EN ISO 10993-15:2000 (composition:NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L). A sample of the material to be analyzed is therefore stored in a sealed sample container with a defined amount of the test medium at 37° C. The samples are removed at intervals of time from a few hours up to several months—coordinated with the expected corrosion behavior—and then are examined for traces of corrosion by known methods. The artificial plasma according to EN ISO 10993-15:2000 corresponds to a blood-like medium and thus represents one possibility for reproducibly simulating a physiological environment in the sense of the present invention.

If the basic body of the stent consists essentially of a biocorrodible magnesium alloy, the lithium salt may then be a component of a coating of the basic body as well as being added as an additive to the implant material. Preferably a basic lithium salt which is soluble in polar organic solvents in particular is used to allow mixing with a polymeric carrier matrix. The lithium salt is selected in particular from the group comprising lithium carbonate, lithium bicarbonate, lithium hydroxide, lithium nitride and a lithium salt of a carboxylic acid compound, e.g., lithium stearate. The special advantage of basic lithium salts in combination with biocorrodible magnesium alloys is that corrosion of the stent implant is inhibited in a basic environment. If the basic body made of the biocorrodible magnesium alloy is provided with a coating consisting of or comprising a polymeric carrier matrix with embedded lithium salt, whereby the carrier matrix is a biocorrodible polymer whose degradation leads to an acidic degradation product, acceleration of degradation of the basic body can be prevented by the presence of basic lithium salts. Furthermore, the risk of rejection reactions can be counteracted by the presence of acidic degradation products of the polymer. The aforementioned negative effects can be compensated or at best reversed if suitable amounts of alkaline lithium salts are released.

If the basic body of the stent consists essentially of a biocorrodible polymer, the lithium salt may be a component of a coating of the basic body as well as being an additive which is added to the implant material. A basic lithium salt is preferably used. Examples of such lithium salts include carboxylic acids, which may also have in particular substituents such as hydroxyl groups or amino groups or may be mixed salts with other cations. Examples of such lithium carboxylates include lithium formate, lithium acetate, lithium lactate, lithium glycinate and lithium bis(oxalato)borate. Lithium acetate is especially preferred, but other basic salts such as lithium carbonate, lithium bicarbonate, lithium hydroxide and lithium nitride may also be used. The use of basic lithium salts is especially preferred when the biocorrodible polymer is a polymer whose degradation leads to an acidic degradation product. The biocorrodible polymer is in particular a polyester, a polyesteramide or a polyanhydride. Due to the addition of basic lithium salts, the risk of rejection reactions due to the presence of acidic degradation products of the polymer can be counteracted.

According to the preceding discussion, other aspects of the present invention include the use of a lithium salt as a coating material for a stent or the use of a lithium salt as an additive for a stent made of a biocorrodible implant material.

EXAMPLES

The invention is explained in greater detail below on the basis of an exemplary embodiment.

Example 1

Coating a Stent

A stent made of the biocorrodible magnesium alloy WE43 (97 wt % magnesium, 4 wt % yttrium, 3 wt % rare earth metals, not including yttrium) is coated as follows:

A solution of lithium bis(oxalato)borate in dimethoxyethane (10 wt %) is prepared at 30° C. This solution is mixed with a second solution of polylactide (L210; Boehringer- Ingelheim) in dimethoxyethane (10 wt %) at room temperature, so that the lithium salt and polylactide form a weight ratio of 1:3.

The stent is cleaned to remove dust and residues and is then clamped in a suitable stent coating apparatus (DES coater, in-house development of Biotronik). Using an airbrush system (EFD or spraying system), the rotating stent is coated on one half side with the lithium salt/polymer mixture under constant ambient conditions (room temperature, 42% atmospheric humidity). With a nozzle spacing of 20 mm, an 18-mm-long stent is coated after approximately 10 min. After reaching the intended layer mass, the stent is dried at RT for 5 minutes before the uncoated side is coated in the same way after rotating the stent and then clamping it again. The finished coated stent is dried for 36 hours at 40° C. in a vacuum oven (Vacucell: MMM).

The layer thickness of the applied lithium salt/polylactide layer is approximately 5 μm.

Example 2

Coating a Stent

A stent corresponding to Example 1 is coated as described below:

A solution of lithium acetate in THF (10 wt %) is prepared at 30° C. This solution is mixed with a second solution of PEGA (polylactide/polyglycolide) in methylene chloride (10 wt %) at room temperature, such that the lithium salt and PLGA are in a weight ratio of 1:4.

The stent is cleaned to removed dust and residues and is clamped in a stent coating apparatus (DES coater, in-house development by BIOTRONIK). With the help of an airbrush system (EFD or spraying system), the rotating stent is coated on one half side with the lithium salt polymer mixture under constant ambient conditions (room temperature; 42% atmospheric humidity). At a nozzle spacing of 20 mm, an 18-mm-long stent is coated after approximately 10 minutes. After reaching the intended layer mass, the stent is dried for 5 minutes a room temperature before the uncoated side is coated on the same side after rotation of the stent and renewed clamping. The finished coated stent is dried for 36 hours at 40° C. in a vacuum oven (Vacucell; MMM).

The layer thickness of the applied lithium salt/PLGA layer is approximately 3 μm.

What is claimed is:

1. A cardiovascular stent having a basic body of an implant material, characterized in that the basic body is coated with a coating consisting of a lithium salt for localized delivery of lithium ions, wherein the lithium salt is selected from the group consisting of lithium carbonate, lithium bicarbonate, lithium hydroxide, lithium nitride and a lithium salt of a carboxylic acid compound.

2. The stent according to claim 1, wherein the implant material comprises a biocorrodible material and a lithium salt.

3. The stent according to claim 1, wherein the lithium salt is basic.

4. The stent according to claim 1, wherein the implant material is a biocorrodible magnesium alloy.

5. The stent according to claim 1, wherein the localized delivery provides a localized lithium ion concentration of 5 to 30 mmol/liter.

6. The stent according to claim 1, wherein the basic body comprises more than 1 wt % and less than or equal to 15 wt % of lithium ions.

7. The stent according to claim 1, wherein lithium content is from 5 to 200 μg per mm stent length.

8. The stent according to claim 1, wherein entire surface of the basic body of the stent is covered by the coating.

9. The stent according to claim 1, wherein the stent is configured to deliver the lithium salt in an amount sufficient to stop a cell cycle in the S-phase at a stented lesion.

10. A cardiovascular stent, the stent having a basic body formed from a biocorrodible magnesium alloy and coated with a coating consisting essentially of a lithium salt dispersed in a polymeric carrier matrix, wherein the lithium salt is selected from the group consisting of lithium carbonate, lithium bicarbonate, lithium hydroxide, lithium nitride and a lithium salt of a carboxylic acid compound, further wherein the basic body comprises more than 1 wt % and less than or equal to 15 wt % of lithium ions.

11. The stent according to claim 10, wherein the coating comprises at least 10% lithium salt.

12. The stent according to claim 11, wherein the coating comprises at least 30% lithium salt.

13. The stent according to claim 10, wherein the body comprises 15 wt % lithium ions.

14. The stent according to claim 10, wherein the lithium salt is the lithium carboxylate, optionally selected from the group consisting of lithium formate, lithium acetate, lithium lactate, lithium glycinate and lithium bis(oxalto)borate.

* * * * *